United States Patent [19]
Johnson et al.

[11] Patent Number: 6,004,759
[45] Date of Patent: *Dec. 21, 1999

[54] METHODS AND COMPOSITIONS FOR DIAGNOSING AUTOIMMUNE INSULIN DEPENDANT DIABETES MELLITUS

[75] Inventors: John H. Johnson; Roger H. Unger, both of Dallas, Tex.

[73] Assignee: Board of Regents, The University of Texas System, Austin, Tex.

[*] Notice: This patent is subject to a terminal disclaimer.

[21] Appl. No.: 07/937,537

[22] Filed: Oct. 6, 1992

Related U.S. Application Data

[63] Continuation of application No. 07/483,224, Feb. 20, 1990, Pat. No. 5,175,085.

[51] Int. Cl.⁶ .................................................. G01N 33/567
[52] U.S. Cl. ........................... 435/7.21; 435/7.8; 436/506; 436/811
[58] Field of Search ..................................... 435/7.21, 7.8; 436/506, 811

[56] References Cited

U.S. PATENT DOCUMENTS 5,175,085  12/1992  Johnson et al. ......................... 435/7.21

*Primary Examiner*—Donna C. Wortman
*Attorney, Agent, or Firm*—Arnold, White & Durkee

[57] ABSTRACT

Disclosed are compositions and methods for diagnosing autoimmune insulin dependent diabetes mellitus. In general, diagnostic methods of the invention include testing for the presence of an autoimmune immunoglobulin in a suspected patient's serum wherein the immunoglobulin is identified by its ability to interfere with the glucose transporting activity of a pancreatic islet cell glucose transporter. The inventors have discovered that the presence of such an autoimmune antibody in patient's serum is diagnostic of autoimmune insulin dependant diabetes mellitus. In particular aspects the diagnostic assay of the invention involves the incubation of isolated and dispersed islet cells, such as rat islet cells, in the presence of immunoglobulin obtained from the patient. Following such an incubation, the islet cells are tested for their ability to uptake glucose. A diagnosis is made through a determination that immunoglobulins in the serum of the patient specifically inhibit the uptake of glucose by the islet cells.

2 Claims, 4 Drawing Sheets

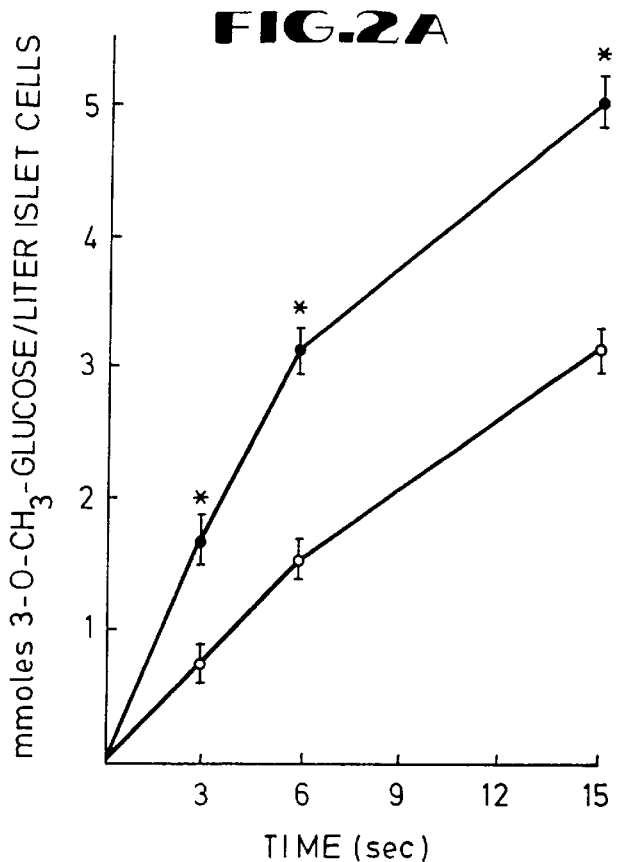
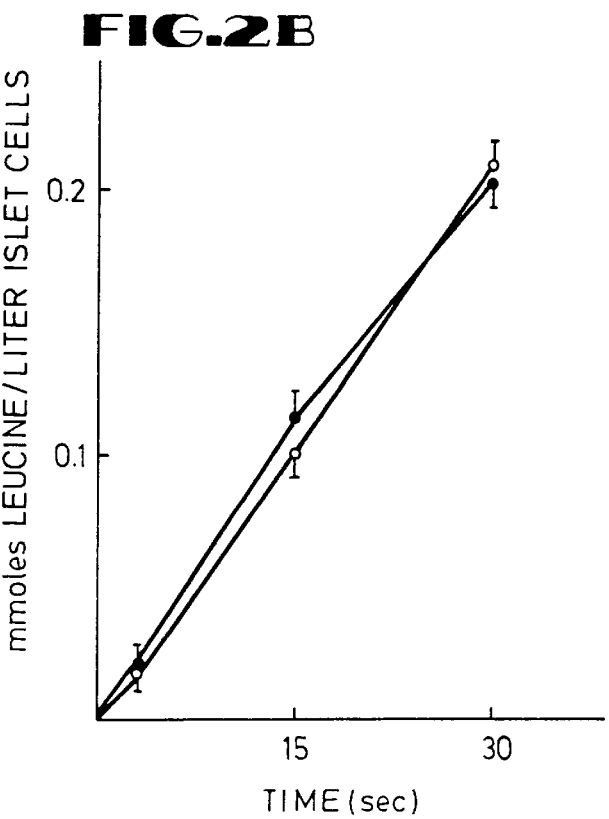

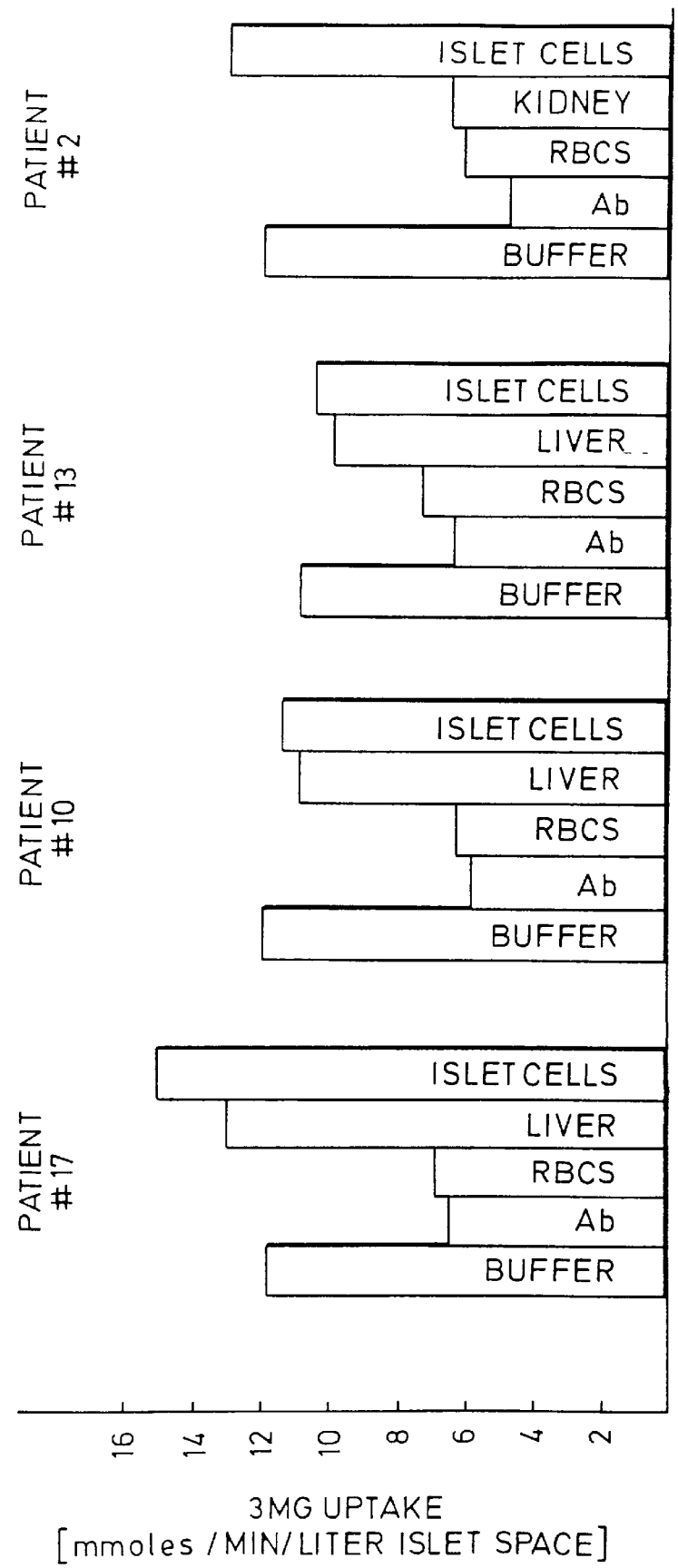

METHODS AND COMPOSITIONS FOR DIAGNOSING AUTOIMMUNE INSULIN DEPENDANT DIABETES MELLITUS

This application is a continuation of U.S. Ser. No. 483,224, filed Feb. 20, 1990, now U.S. Pat. No. 5,175,085.

The Government may own certain rights in this invention pursuant to NIH Grant AM-02700.

BACKGROUND

1. Field of the Invention

The present invention relates to compositions and methods for diagnosing autoimmune insulin dependent diabetes mellitus (IDDM). In particular, the invention concerns the diagnosis of IDDM through the detection of a particular autoimmune immunoglobulin (Ig) in patient sera, an Ig which interferes with a pancreatic islet cell-localized glucose transporter.

2. Description of the Related Art

Insulin Dependent Diabetes Mellitus ("Type I") represents 20% of all human diabetes, and is the most serious form of the disease, with the highest morbidity and mortality. Progression of the disease is associated with a major loss of pancreatic islet β cell function and cell destruction (1). This loss of pancreatic β cells which is apparently quite cell-specific in its early stages since other cell populations which comprise the islets of Langerhans (α cells, δ cells) are unaffected (2).

The series of autoimmunologic events which give rise to IDDM, or which are otherwise involved with IDDM onset, are poorly understood. However, the disease involves a progressive reduction in the function of pancreatic islets of Langerhans β cells. It has, for example, been reported that a preferential loss of insulin response to glucose occurs without a corresponding reduction of the response to certain non-glucose secretagogues, such as amino acids or isoproterenol, during development of IDDM (3).

Currently available diagnostic procedures such as blood and urine determinations diagnose IDDM only after the onset of symptomatology associated with the disease, when β cell destruction is almost complete. This reduces or eliminates an ability to initiate intervention early on, when it is theoretically possible to arrest the destructive process. For this reason, a simple, rapid, and inexpensive diagnostic test capable of correctly identifying a IDDM patients prior to the onset of clinical disease is needed. Currently, islet cell antibodies and insulin autoantibodies identify only about 60% of such patients.

An autoimmune etiology has been implicated in a large percentage of IDDM cases, which have led researchers to try to identify a particular target or antigen. For example, Kanatsuna et al. have reported that plasma obtained from IDDM patients soon after onset will inhibit glucose-stimulated insulin secretion by rat islets (4). Furthermore, the results from several studies employing various techniques, including immunofluorescence on tissue section, chromium[51]-release, etc., have demonstrated that antibodies reactive with pancreatic islet cells are often present at the time of diagnosis of IDDM (1). Other studies have identified antibodies to a 64 kd islet membrane protein, said to be detectable prior to the onset of clinical disease, in 73% of new onset IDDM patients (6–8). However, no biological function has been ascribed this antigen, and it has not as yet been isolated or further characterized.

For the foregoing and other reasons, a need exists for a diagnostic test for IDDM that addresses one or more of the problems associated with previously available tests. For example, a test that can predict the potential for IDDM development prior to its onset, thus allowing time for intervention therapy would prove particularly useful, as would a test capable of faithfully identifying pre-onset IDDM patients with a high sensitivity. It is believed that the present invention, directed to methods for the detection of particular autoimmune antibodies, addresses at least some of these or other disadvantages associated with previous approaches to IDDM diagnosis.

SUMMARY OF THE INVENTION

The present invention is directed in general to the diagnosis of autoimmune Type I diabetes (IDDM) through the detection of a particular class of autoimmune immunoglobulins—those having immunospecificity for a pancreatic islet β-cell glucose transporter, or for a separate, functionally associated protein. The islet β-cell glucose transporter or associated protein, while apparently similar in function to other transporters, is immunologically distinct from those found in skeletal muscle, red blood, adipocyte-containing tissue, and even brain tissue. The invention evolves out of the inventors discovery that such antibodies are associated with the onset of IDDM and can be used as early diagnostic indicators of the disease. The invention has the surprising and unique feature of detecting, in a single assay, immunological and functional abnormalities. This is so since neutralization of the antigen, the glucose transporter, by the antibody may cause the functional defect in insulin secretion.

During their development of the invention, the inventors proposed that an early event in the onset of IDDM is the appearance of anti-β cell immunoglobulins which react with β-cell- and liver cell-localized glucose transporter or functionally associated protein. This anti-glucose transporter is believed to bind to the transporter and thereby sterically hinder or otherwise interfere with the uptake of glucose by β-cells. The resultant lack of glucose greatly compromises the β-cell and ultimately leads to a selective loss of β-cell function, as well as β-cells themselves.

The invention is thus directed in part to a method for diagnosing autoimmune insulin dependent diabetes mellitus (IDDM) which includes testing the sera of a suspected diabetic or candidate for early onset diabetes, for the presence of an autoimmune immunoglobulin identified by its ability to interfere with the glucose transporting activity of pancreatic islet cells. The inventors have discovered that the presence of such an antibody in a patient's serum is diagnostic of Type I diabetes, and it is believed to be an early diagnostic indicator of subsequent development of diabetes.

As used herein, the phrase "islet cell glucose transporter" refers to one or more of the protein or proteins which take part in the facilitated transport of glucose into islet β-cells. The term is also intended to include associated structures—perhaps sterically associated in terms of a proximal location, for example, on the β-cell surface—so long as the structure comprises antigenic epitopes which, when recognized and bound by autoimmune antibodies, results in the suppression of glucose uptake. Such epitopes may be natural antigenic epitopes of the glucose transporter. Alternatively, such epitopes may be synthetically produced to mimic antigenic regions of the glucose transporter, and, in any case, will stimulate production of antigen capable of interrupting transport of glucose into islet β-cells.

In certain embodiments, testing for the presence of an anti-β-cell glucose transporter include steps of 1) preparing an admixture of the islet cell glucose transporter together with immunoglobulin (Ig) from the patient; 2) incubating the admixture under conditions appropriate for the formation of immunocomplexes; and 3) testing for the formation of immunocomplexes between the islet cell glucose transporter and the patient's Ig, indicative of the presence of the anti-β cell glucose transporter Ig in the patient's sera.

In particular aspects, testing for the anti-transporter autoimmune immunoglobulin includes testing for a relative inhibition of the rate of glucose uptake by the islet cells, with such an inhibition indicating the presence of the anti-transporter antibody. This embodiment relies upon an ability to assay for glucose transporter biologic activity. This arises out of the inventors observation that the rate of glucose uptake, particularly the initial rate, is relatively inhibited in the presence of the anti-transporter immunoglobulin. The term "relatively inhibited" is intended to refer broadly to inhibition "relative" to some control, such as the inhibition of the islet cell antigen as compared to non-islet cell, by techniques such as comparison of the patient's immunoglobulin to a control immunoglobulin preparation, or by comparison of the uptake of glucose in relation to a control metabolite or the like.

In certain aspects, a biological assay is employed to test for the presence of antibodies having anti-glucose transporter activity, e.g., plus and minus incubation with patient's immunoglobulins. In these instances, one will desire to obtain the transporter in a biologically active form. The inventors have found that the most convenient means is to simply employ isolated rat islet cells, obtained, e.g., following collagenase digestion of rat pancreas and Ficoll gradient purification. Isolated rat islet cells can be readily used to measure glucose uptake in connection with the practice of the present invention in that the rat β-cell transporter is apparently immunocrossreactive with the human transporter. Thus, the rat islet cell transporter is recognized, and inhibited, by human anti-β-cell glucose transporter immunoglobulins. Other embodiments of biologically active glucose transporter may be employed in place of rat islet cells, including glucose transporter expressed in non-β-cells or synthetically (9).

It is preferable to prepare immunoglobulin G (IgG) from the patient's sera prior to testing for the antibody. This is due to possible interfering substances which may be present in the patient's sera or Ig and can give a high background or reduced sensitivity or selectivity to the assay. Using purified IgG is particularly desirable where a bioassay is to be performed. In that the autoimmune Ig identified in connection with the present invention will generally be IgG, the use of the IgG fraction in assays hereof is to be encouraged. IgG of suitable purity has been routinely obtained by the inventors by purification of sera on a protein A Sepharose column (10). Of course, other suitable methods for preparing IgG are known and these could be successfully employed, including polyetheneglycol precipitation and ammonium sulfate fractionation (4).

Glucose uptake may be concomitantly measured through the use of a readily identifiable glucose analog that will function as a substrate for the transporter. Exemplary analogs, particularly useful in connection with the present invention, are those which can incorporate detectable ligands, radioactive groups, $H^3$, $C^{14}$ and the like. A preferred analog is 3-0-methyl-β-D-glucose which is both easy to prepare and into which such detectable ligands can readily be introduced. While 3-0-methylated analogs are preferred, other analogs or substrates could be employed if desired, such as 2-deoxy-glucose.

Individual points on each curve represent the mean±SEM from duplicate determinations made in six independent experiments. Uptake measurements were performed on dispersed cells from 250 islets for each time point.

FIGS. 2A and 2B. Effects of purified IgG from normal humans (open circles) and new-onset IDDM patients (closed circles) on the uptake of 3-0-methyl-β-D-glucose and L-leucine by dispersed rat islet cells.

FIG. 2A. Uptake of 3MG by islet cells after treatment with IgG from normal humans (n=28) and new-onset IDDM patients (n=27).

FIG. 2B. Uptake of L-leucine by islets after treatment with IgG from normal humans (n=15) and new-onset IDDM patients (n=9).

Uptake assays were performed using coded IgG samples. Samples were decoded and data from duplicate determinations at each time point for each individual IgG sample were segregated into diagnosis groups and used to determine the mean±SEM of uptake at each time point shown in the curves. L-leucine uptake was measured on the same islet preparation as 3MG uptake for the indicated number of IgG samples. The statistical differences in the time points of the curves is indicated by an (*) where p<0.01.

Figure 3:
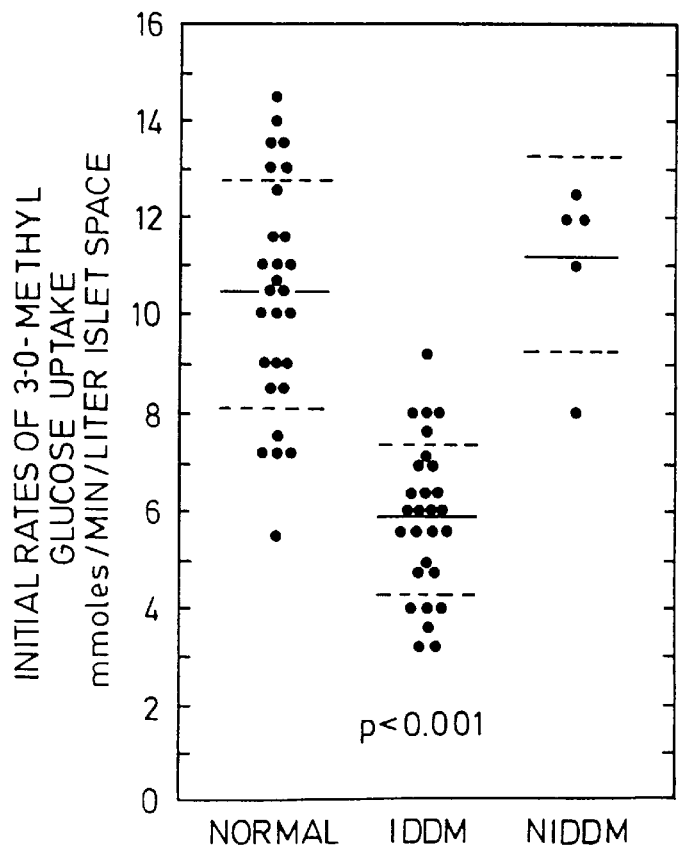

FIG. 3. Distribution of the initial rates of 3-0-methyl-β-D-glucose uptake by rat islet cells in the presence of IgG from each individual after segregation in to diagnosis groups.

Initial rates of uptake of 3MG uptake were determined as described in the Methods sections for each IgG sample from 28 normal humans, 27 IDDM patients, and 5 NIDDM patients. The horizontal solid line is the mean 3MG uptake in the presence of IgG from each group and the dashed line represents one standard deviation from the mean in each group.

Figure 4:
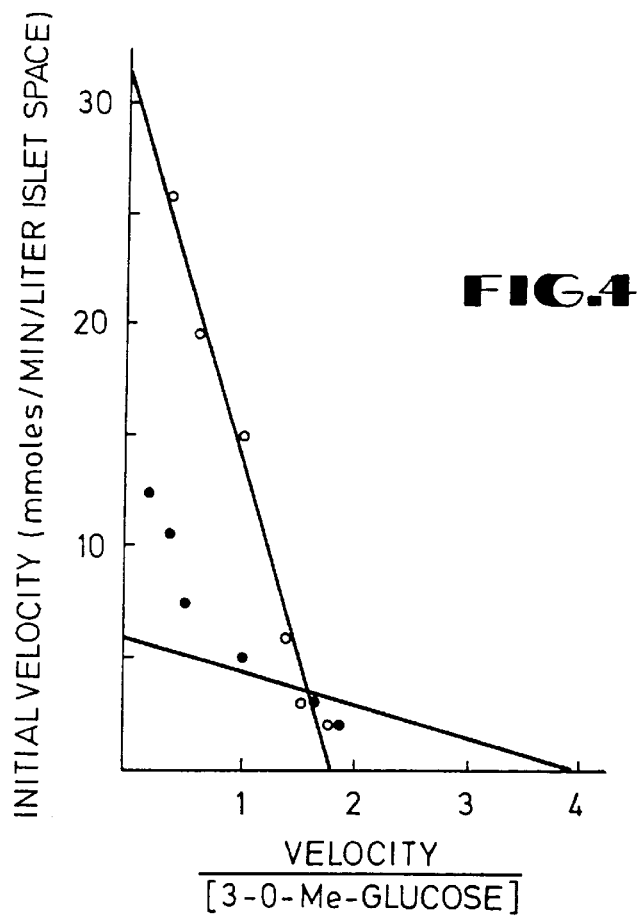

FIG. 4. Effects of IgG from Normal Subjects (open circles) and New-Onset Patients (closed circles) on the Glucose Concentration Dependence of Glucose Uptake by Rat Islet Cells.

The initial rates of 3-0-methyl-β-D-glucose uptake were determined as described in Methods. The islet cells were incubated with IgGs from 3 normal subjects (open circles) and 3 IDDM patients (closed circles) and 3-0-methyl-β-D-glucose uptake was measured at 60, 30, 15, 5, 2, and 1 mM 3-0-methyl-β-D-glucose concentrations. The results are presented as the Eadie-Hofstee transformation of the mean initial velocity measurements. The solid lines represent the results obtained with islet cells assayed in buffer alone.

Figure 5A:
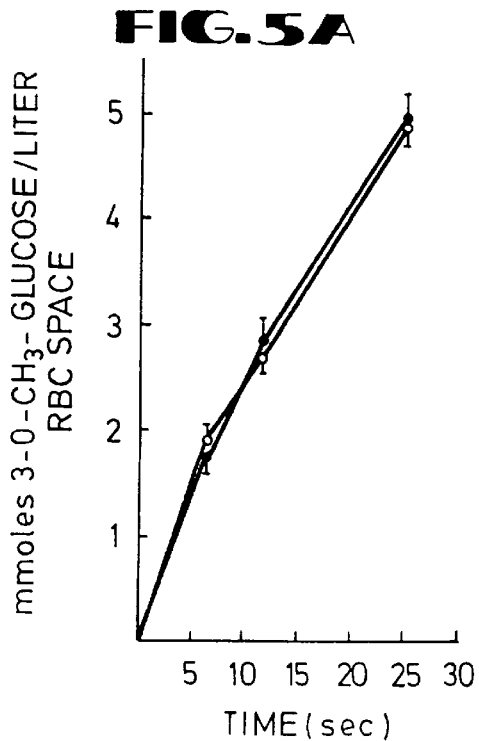
Figure 5B:
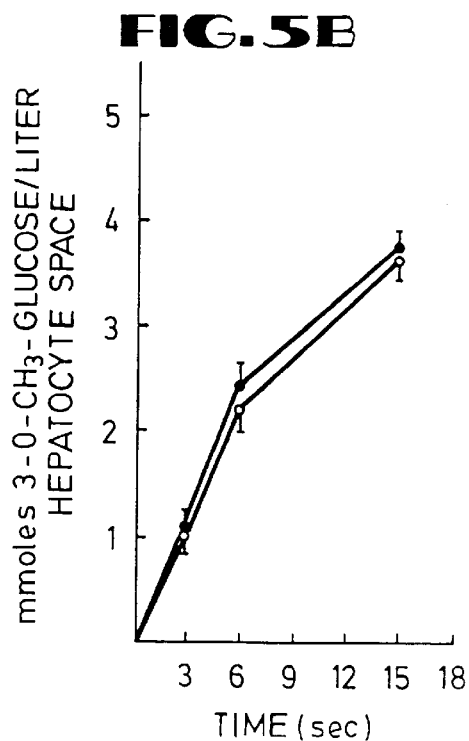

FIGS. 5A and 5B. Effects of IgG fractions from normal subjects (open circles) and IDDM patients (closed circles) on the uptake of 3-0-methyl-β-D-glucose by human erythrocytes (FIG. 5A) and rat hepatocytes (FIG. 5B).

Uptake of 3MG was measured as described for islet cell uptake using IgG preparations from normal subjects and 3 IDDM patients. The results shown are the mean±SEM values for each time point.

FIG. 6. Effect of preincubation of IgG from IDDM patients with cells or cell membranes from islets, liver, erythrocytes, or kidney brush border on 3-methyl glucose uptake by islet cells. The preparation of the membranes and their incubation with the IgG fractions are described in detail in the Methods section. Ab is uptake in the presence of IgG not preincubated with any tissue preparation.

DETAILED DESCRIPTION OF THE PREFERRED EMBODIMENTS

Autoimmunity and a progressive loss of β-cell function are features of insulin-dependent diabetes mellitus (IDDM). In the development of the invention, characteristics such as these led the inventors to consider that a part of the glucose recognition apparatus of β-cells was involved in the autoimmune response. Contrary to many existing theories (4), it was considered by the inventors that a target of the autoimmune response was a pancreatic β-cell-localized glucose transporter, recognized by autoimmune antibodies in connections with the onset of the disease. A series of studies have been conducted by the inventors which support a conclusion that the glucose transporter, or perhaps a physically or functionally associated antigenic structure, is indeed an autoimmune target in new onset IDDM.

In an exemplary set of studies, set forth herein, the uptake of 3-0-methyl-β-D-glucose by dispersed rat islets of Langerhans was measured after treatment with IgG obtained from 28 control humans, 27 new-onset IDDM humans and 5 noninsulin-dependent diabetic (NIDDM) humans. In 26 of 27 (94%) IgG fractions from IDDM patients, initial rates of 3-0-methyl-β-D-glucose uptake were found to be inhibited below one standard deviation from the mean of controls ($p<0.001$). This effect was not a general permeability decrease as there was no effect on L-leucine uptake by islet cells after treatment with these IgG fractions. Further, the IgG fractions from IDDM patients did not inhibit uptake of 3-0-methyl-β-D-glucose by human erythrocytes or rat hepatocytes. These studies demonstrated that IgG from humans with new-onset IDDM inhibits glucose uptake by rat islet cells by recognizing the glucose transporter of these cells or an unrelated protein which is involved structurally or functionally in islet cell glucose transport.

In more particular terms, the method of invention involves testing for the presence of an autoimmune immunoglobulin in serum of a patient suspected of having autoimmune IDDM, wherein the immunoglobulin is identified by its ability to interfere with the glucose transporting activity of pancreatic cell glucose transporter. The presence of such an immunoglobulin in the patient serum has been found by the inventors to be diagnostic of autoimmune IDDM. Most conveniently, the assay is performed by testing for the presence of immunoglobulins that are capable of inhibiting glucose transport function in isolated islet cells. Preferably, islet cells are isolated from rat pancreata and dispersed to form an essentially single cell suspension. Ideally a cell suspension is prepared wherein cell aggregation is minimized. In that it has been found that maintenance of cell viability is important to the successful practice of the preferred method of the invention, it may be desirable to determine cell viability by a procedure such as fluorescein diacetate uptake, or uptake of another vital dye which is indicative of a functional cell membrane transport system and therefore viability. Typically one will desire to obtain at least about 70% of the cells as viable cells, and more preferably at least about 70% viable cells.

Following isolation and dispersion of islet cells, the cells are incubated in the presence of an antibody solution prepared from sera of the patient to be tested. Preferably, the dispersed cells are incubated with a immunoglobulin G (IgG) fraction prepared from the patient's sera. While more conventional methods of IgG preparation such as ammonium sulfate fractionation can be employed to prepare IgG, a more preferred approach involves the use of a protein A-Sepharose or like adsorbent. Protein A-Sepharose chromatography has been found to provide a simple and expedient means for obtaining relatively purified IgG. While the use of IgG is preferred, it is believed by the inventors that total immunoglobulin or even serum may be used directly in the assay if desired. In any event, in initial incubations with isolated islet cells one will typically desire to employ patient antibody-containing compositions at a concentration wherein the IgG concentration in the final incubation admixture will be on the order of 5–15 mg/ml, and preferably about 8–10 mg IgG/ml. This will represent approximately $10^6$ islet cells per mg IgG.

In the measurement of glucose uptake by the dispersed cells, one may desire to incubate the dispersed cells in an antibody solution together with a labeled indicator or marker which will allow one to determine intracellular space. An example of such a marker of intracellular space is urea, which will penetrate the cells and occupy total intracellular space in a non-facilitated fashion. By measuring the uptake of an intracellular space marker such as urea, one is able to determine the total amount of intracellular space into which the glucose to be subsequently measured is taken up. Such a measurement, while not crucial to the practice of the invention, allows one to determine with greater precision the measurement of glucose uptake. Other suitable intracellular space markers are well known in the art and include, for example, urea or water, or the like.

Following incubation with an intracellular space marker, the cells are further incubated in the presence of the selected glucose analogue. A preferred analogue is 3-0-methyl-β-D-glucose in that this analogue can be readily prepared and is taken up by viable cells in a facilitated fashion just as glucose itself is but is not metabolized by these cells while glucose is metabolized. In preparing the selected glucose analogue, one will generally desire to incorporate a ligand that is distinct from the intracellular marker, where one is employed. The reason for this is to allow one to separately measure the glucose uptake in relation to the intracellular space. Thus, for example, one may desire to employ a $C^{14}$ ligand in connection with an intracellular space marker such as urea and a $H^3$ ligand in connection with the glucose analogue.

Glucose uptake may be initiated by admixing an antibody-incubated cell suspension with the glucose analogues for a selected period of time. It may be desirable to terminate uptake by sedimenting the cells through a hydrophobic phase, such as a dibutyl/dinonyl phthalate phase, into a cushion such as a glucose cushion by centrifugation. Such a procedure is desirable in that it separates only viable cells for uptake measurement and minimizes extracellular space which can interfer with the precision of the measurement.

Following termination of incubation, uptake determinations may be made through scintillation counting of the cells. The uptake of separate isotopes, corresponding to intracellular space and glucose uptake, respectively, thus may be determined by reference to the scintillation counter window that is appropriate for the particular isotope. Where both $C^{14}$ and tritium are employed, respectively, one will desire to obtain a counting of the incubated cell material in both a tritium and a $C^{14}$ window of the counter.

In that one will generally desire to measure the initial rates of glucose analogue uptake, uptake is measured at selected intervals following initiation of glucose uptake. It has been found that time points in the 3 to 15 second time frame, measured from an initiation of glucose uptake, is most preferred. The determination of initial rates of glucose uptake have been found by the present inventors to reflect the most reliable means of detecting the presence of the anti-transporter antibody in the patient's serum. Measurements taken at, e.g., time points such as 3, 6 and 15 seconds of incubation, can then be expressed in terms of a mean for each point.

A determination of the relative reduction in the initial rate of glucose uptake can be performed by comparing the inhibition of glucose uptake by islet cells treated with IgG from suspect patients to glucose uptake by islet cells treated with IgG from known normal individuals. As a second level of assessment, one can compare the inhibition of glucose uptake and islet cells versus the uptake of a metabolite that is taken up by islet cells by transport other than by the glucose transporter. In such an embodiment the uptake of glucose will be inhibited by the anti-transporter antibody whereas the uptake of the non glucose metabolite will not. Suitable metabolites which can serve as uptake controls include amino acids such as L-leucine, L-arginine, or L-alanine. Other useful metabolites include ions, organic acids, or the like.

Therefore, to determine the control uptake, whether it be a glucose uptake by non-islet cells or a non-glucose metabolite uptake by islet cells, control assays may be run in parallel with assays measuring islet cell glucose uptake. The uptake determined for controls are then compared to the uptake determined for islet cell glucose uptake. From this comparison it is determined whether there is a relative inhibition of glucose uptake in the presence of the suspected patient's immunoglobulin.

For the purposes of the present invention, it is believed that a relative inhibition of on the order of 30 to 70%, will indicate the presence of an anti-transporter immunoglobulin in the patient's serum. Generally, one will see an inhibition of on the order of 50% in such patients. However, it is believed that inhibitions of on the order of 30 to 70% are useful indicators of the anti-transporter antibody in such ranges as submitted to be diagnostic of the disease.

The following example illustrates various preferred embodiments for carrying out the invention. The studies set forth below were conducted in part through the application of standard laboratory practices of the inventors as well as procedures developed by the inventors or found to work well in the practice of the invention. Various modifications, rearrangements of steps substitutions and the like, will be apparent to the skilled artisan in light of the examples which follow.

DIAGNOSIS OF AUTOIMMUNE IDDM USING DISPERSED RAT ISLET CELLS

A. Procedures Employed

1. Patient Populations

Serum for IgG purification was obtained from 27 new onset IDDM patients (ages 6–34), 28 nondiabetic controls (ages 22–64) and 5 patients with NIDDM (ages 55–64). In the IDDM patients the serum was obtained within 2 months of diagnosis; in 1 patient the diagnosis had been made 8 months earlier. Each serum was assigned a code number by an outside colleague and all subsequent work was performed on coded specimens. The IgG fractions from all diabetic patients were tested for the presence of cytoplasmic islet cell antibodies using the method of Krell & Rabin (9).

2. Immunoglobulin G (IqG) Purification

Protein A-Sepharose (Pharmacia Fine Chemicals, Uppsala, Sweden) was prepared by extensive washing and pre-equilibration with 0.1 M sodium phosphate, pH 7.0. Sera from patients were diluted with an equal volume of 0.1 M sodium phosphate pH 7.0 and 4 ml of sample were mixed with 2 ml Protein A-Sepharose. Following 30 minute incubation with inversion mixing at room temperature, the suspension was transferred to a column and washed with 20 ml of 0.1 M sodium phosphate, pH 7.0. IgG was eluted from the column using 10 ml of 0.5 M acetic acid in 0.89% saline pH 3.0. During elution of antibody from the column, the pH of the eluted was monitored and immediately adjusted to pH 7.0 with 3.3 M Tris hydroxyamino methane (free base). The eluate was concentrated and dialyzed against phosphate-buffered saline. IgG concentrations used in this study were $9.0 \pm 0.3$ mg/ml, which represents approximately $10^6$ islet cells per mg IgG.

3. Islet Isolation and Dispersal

Islets for each experiment were isolated from the pancreata of 15–20 male Wistar rats (200–250 g) using a modification of the method of Naber et al. (12). Briefly, pancreata were inflated with 20 ml of chilled Hanks balanced salt solution (HBSS) containing 0.5% bovine serum albumin and the digested material was washed three times in HBSS containing 0.5% BSA. The final sediment was resuspended in 4 mls 25% Ficoll in HBSS and was overlaid with 2 mls each of 23%, 20.5% and 11% Ficoll (w/w). Gradients were centrifuged at 700× g for 15 minutes at 4° C. and islets were harvested from the 11%/20.5% interface with a plastic pipet. Ficoll was removed by washing the islets with HBSS containing 0.5% bovine serum albumin by centrifugation at 700 kg for 2 minutes at room temperature. From 5000 to 8000 islets were routinely obtained from 20 rats.

Purified islets were resuspended in $Ca^{2+}$, $Mg^{2+}$-free HBSS containing 3 mM ethyleneglycol-bis-(β-amino ethyl ether) N, N'tetracetic acid (EGTA) and incubated at 37° C. for 15 minutes. During incubation, islets were subjected to gentle aspiration into and out of a plastic pipet. This procedure yielded a cell suspension which was mostly single cells with a few three to five cell aggregates. Fluorescein diacetate uptake revealed that $70 \pm 5\%$ of the cells were viable (13).

4. Uptake Measurement

Dispersed cells from 3500 islets were incubated in 0.7 ml antibody solution containing a final concentration of 2 mM [$^{14}$C] urea (0.5 μCi/μmole) as an intracellular space marker at 37° C. for 20 minutes. Cells were further incubated for 10 minutes at 15° C. before assay of uptake. Uptake of glucose analogues was determined using a modification of the method of Gorus et al. (14).

3-0-methyl-β-D-glucose was prepared as follows: 50 μl of 1 M glucose containing 10 mM EDTA and 0.1% sodium dodecylsulfate (SDS), pH 8.0 was placed in the bottom of 400 μl microfuge tubes. This solution was overlaid with 150 μl of a dibutyl phthalate/dinonyl phthalate (4:1) mixture. Following 30 seconds of centrifugation in a Beckman microfuge, 50 μl of phosphate-buffered saline containing [$^{14}$C] urea (2 mM, 0.5 μCi/μmole) and 20 mM 3-0-β-D [$^3$H] methyl-glucopyranoside (5 μCi/μmole) was layered over the dibutyl/dinonyl phthalate phase. The tubes were then pre-incubated for 20 minutes at 15° C.

Uptake of the glucose analogue was initiated by adding 50 μl of the cell suspension preincubated with urea to the 50 μl phosphate-buffered saline phase containing labeled glucose analogues and urea. Uptake was terminated by starting the microfuge and sedimenting the cells through the dibutyl/dinonyl phthalate phase into the 1 M glucose, 10 mM EDTA, 0.1% SDS. A 50 μl portion of the supernatant was removed from each tube for specific activity calculations and a 35 μl portion of the 1 M glucose, 10 mM EDTA, 0.1% SDS phase was removed for uptake determination and counted in a Beckman LS 5801 liquid scintillation counter.

Uptake was measured in duplicate for the times indicated in each experiment. Data were reduced to dpm for each isotope using the resident calculation program of the counter and were expressed as mmoles/liter islet space. Corrections for extracellular space as judged by zero-time L-glucose measurements were 19, 22 and 28 percent of the total urea space in experiments performed in buffer alone, buffer containing IgG from normal humans, and buffer containing IgG from IDDM patients, respectively. Initial rates of 3MG uptake were derived from the 3, 6, and 15 second time points. Measurement of L-[1, $^3$H] glucose and L-[3,4,5,$^3$H]-leucine uptake were made using the same procedure. Data are expressed as mean±standard error of the mean (SEM) for each time point.

5. Statistical Analyses

Data were decoded, segregated according to diagnosis and compared by using an unpaired two-tailed t-test. The mean±SEM for all data are reported in cumulative time courses and initial rates of substrate uptake.

6. Adsorption of IgG Preparations

Adsorption studies were carried out to determine if the glucose transport inhibitory activity of the IgG fractions was abolished by preincubation of with various tissues that contain glucose transporters similar or dissimilar to β-cells. We prepared unsealed red blood cell ghosts (13), liver plasma membranes (14), and kidney brush border specimens (15). The IgG preparations were diluted to 4 mg IgG/ml in phosphate-buffered saline and incubated with dispersed islet cells from 40 rats (~20,000 islets), 20 mb liver plasma membrane protein, 20 mb rat red blood cell ghost protein, 20 mg kidney brush border membrane protein or buffer alone for 3 hr at 4° C. The mixtures were then centrifuged at 800× g for 5 minutes and twice at 50,000× g for 10 min to remove islet cells or membranes. The supernatants were carefully removed and stored at 4° C. overnight, after which they were added to dispersed rat islet cells. Following incubation the cells were assayed for 3MG uptake as described above.

B. Results of the Studies

1. Clinical Composition of Patient Populations

The sex. age. diagnosis, treatment and islet cell antibody status of all IDDM patients are shown in Table 1.

TABLE 1

Characteristics of Diabetic Patients and Normal Subjects

| Patent Type 1 | Sex | Age (years) | Islet Cell Antibody (cytoplasmic) |
|---|---|---|---|
| 1 | M | 19 | + |
| 2 | M | 7 | + |
| 3 | M | 13 | + |
| 4 | M | 10 | + |
| 5 | F | 8 | + |
| 6 | F | 7 | + |
| 7 | F | 11 | + |
| 8 | F | 8 | + |
| 9 | F | 7 | + |
| 10 | F | 8 | + |
| 11 | M | 12 | + |
| 12 | M | 14 | + |
| 13 | F | 24 | + |
| 14 | M | 6 | +/− |
| 15 | M | 11 | +/− |
| 16 | F | 7 | − |
| 17 | F | 11 | − |
| 18 | F | 11 | − |
| 19 | F | 13 | − |
| 20 | M | 9 | − |
| 21 | F | 12 | − |
| 22 | M | 19 | − |
| 23 | F | 8 | − |
| 24 | F | 12 | − |
| 25 | M | 6 | − |
| 26 | M | 34 | − |
| 27 | F | 27 | − |

| | Mean Values ± | |
|---|---|---|
| IDDM Patients (N = 27) | 12 M/15 F | 12.4 ± 6.8 |
| NIDDM Patients (N = 5) | 3 M/2 F | 57.0 ± 5.6 |
| Normal Subjects | 18 M/10 F | 35.8 ± 10.3 |

All type 1 patients were treated with NPH insulin.
The diagnosis of NIDDM diabetes in patients #26, and 27, the two oldest patients was based on a history of ketoacidosis.
Three of the NIDDM patients were receiving gliburide and were receiving NPH insulin.

2. Glucose Uptake by Islet Cells

Figure 1:
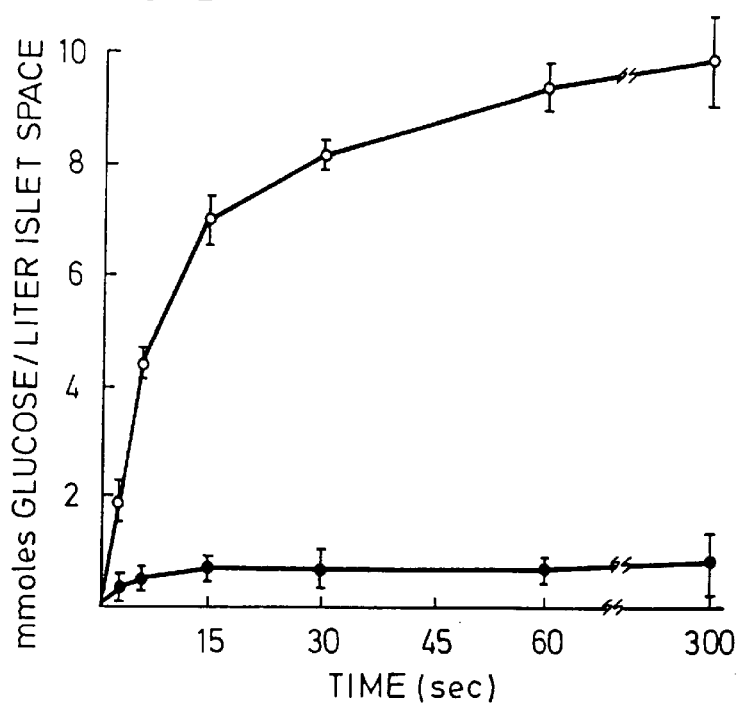
FIG. 1 Time course of the uptake of 3-0-Methyl-β-D-Glucose (open circles) and L-Glucose (closed circles) by Dispersed Rat Islet Cells.

As shown in FIG. 1, the uptake of 3MG by islet cells, was consistent with facilitated diffusion. The half time was less than 15 seconds and equilibrated with the extracellular 3MG concentration was more than 90% complete in 1 minute (FIG. 1). By virtue of the stereospecificity of known glucose transporters, L-glucose should be excluded from intact cells (14–16). In these studies L-glucose uptake at time zero was 19.2% of the urea space, increased slightly through 6 seconds and did not change thereafter, thus providing evidence that the permeability barrier of the islet cells was intact (FIG. 1). L-glucose uptake was therefore determined at time zero in subsequent studies to provide an index of the extracellular space and cellular integrity.

3. Effects of IgG on 3MG Uptake into Islet Cells

An initial comparison of IgG from the first 8 participating IDDM patients and 11 controls revealed significant inhibition of 3MG accumulation at 3, 6, 16 and 30 seconds (p<0.01) but not at later time points. As would be expected in an incompletely inhibited facilitated diffusion transport system, inhibition was greatest at the earliest time points. Subsequent comparisons in additional subjects were therefore restricted to the 3, 6 and 15 second time points which provide the most accurate estimation of the initial rate of uptake. IgG from 27 new-onset IDDM patients was found to inhibit significantly (p<0.01 at each time point) 3MG transport in dispersed rat islet cells compared to 28 control subjects (FIG. 2a). Progressive dilution of IgG resulted in progressive loss of this inhibitory activity.

L-leucine uptake (FIG. 2b) was measured in tandem using IgG from 9 IDDM patients and 15 control subjects to determine if the inhibition was restricted to 3MG transport or if inhibition of 3MG uptake represents a nonspecific permeability alteration in islet cells exposed to islet cell antibodies. Uptake of L-leucine was virtually identical in islet cells incubated in IDDM and control IgG.

The distribution of individual initial rates of 3MG uptake from all determinations using 28 nondiabetic, 27 IDDM and 5 NIDDM IgG preparations is compared in FIG. 3. In islet cells incubated with IgG from patients with IDDM, initial rates of 3MG transport derived from the 3, 6, and 15 second time points were 50% below control values (p<0.001). The rates in islet cells incubated with IgG from patients with NIDDM and other autoimmune diseases (w patients with Graves disease and 1 with systemic lupus erythematosus)

(not shown) were similar to the rates in the presence of IgG from normal subjects. Reproducibility of the initial rate determinations were {1.8 mmoles 3MG min$^{-1}$ liter islet space$^{-1}$ from 9 experiments using different IgG preparations from 4 IDDM patients. Data in FIG. 3 include only the first determination of each individual and do not include replicate experiments.

4. Effects of IgG on 3MG Concentration Dependence of 3MG Uptake

Examination of the glucose concentration dependence of 3-0-methyl-β-D-glucose uptake by the islet cells used in this study revealed the presence of two kinetically distinct facilitated diffusion transporters; one with an apparent Km of 18 mm and another with an apparent Km of 1.5 mM (J. H. Johnson, unpublished results). The Km 18 mM transporter is kinetically similar to the liver transporter and studies with an antibody to the liver transporter indicate that in the pancreas the antibody is localized to β-cells (14,18). To test whether the IgG fractions from IDDM patients affects glucose transport by exerting their effects preferentially on the Km 18 mM transporter or the Km 1.5 mM transporter of β-cells, the glucose concentration dependance of 3-0-methyl-β-D-glucose uptake was measured in islet cells incubated with IgG from 3 IDDM patients and 3 normal subjects. FIG. 4 shows that the IgG fractions from the IDDM patients inhibited β-cell Km 18 mM transport activity without affecting Km 1.5 mM transport. The IgG fractions from the normal subjects did not alter these kinetics. Furthermore, the IgG from the IDDM patients decreased the maximum velocity of uptake without altering the Km. These data further support an interaction between the IgG and β-cell glucose transporters.

5. Effects of Insulin and Insulin Antibodies upon 3-0-Methyl-β-D-Glucose Uptake by Normal Rat Islet Cells The IgG fractions from the IDDM patients, all of whom had been treated with insulin for several weeks, may well have contained insulin antibodies (19) and/or autoantibodies (20) not present in the IgG fractions from the normal subjects. To exclude the possibility that such antibodies might influence glucose uptake, 3-0-methyl-β-D-glucose uptake was measured in the presence and absence of guinea pig anti-insulin serum. The guinea pig anti-insulin serum had no effect on islet cell 3-0-methyl-β-D-glucose uptake rates being 9.8±0.8 mmoles/min/liter islet cell space in the presence of anti-insulin antibody (10 μg/ml, n=3) compared to 11.3±0.8 mmoles/min/liter islet space in the presence of buffer. The possibility that insulin copurified with insulin-binding antibodies might bind to islets cells and somehow alter glucose transport was also tested. The uptake rates of cells retreated for 20 min. with both insulin and anti-insulin antibody took up 3-0-methyl-β-D-glucose at a rate of 10.2±1.1 mmoles/min/liter islet space. Therefore, neither insulin nor anti-insulin antibody nor the combination affected islet cell 3-0-methyl-β-D-glucose uptake.

6. Effects of IgG on 3-0-Methyl-β-D-Glucose Uptake by Erythrocytes and Hepatocytes Recent evidence indicates that several structurally distinct facilitated diffusion glucose transporters exist in mammalian tissues. The glucose transporter from erythrocytes, adipocytes, and brain differs from the transporter found in liver (21), whereas antibodies to a synthetic 13 amino acids peptide from the predicted sequence of the C-terminal region of the 55 kd rat liver glucose transporter reacts with a transporter expressed in β-cells (18,21). The IgG fractions from 4 IDDM patients did not inhibit 3-0-methyl-β-D-glucose uptake into human erythrocytes by also failed to inhibit uptake by tat hepatocytes, despite the apparent similarity of liver and β-cell glucose transporters (FIG. 5).

7. Effects of Preincubation of IgG from IDDM patients with Islet-cells and Liver, Erythrocyte and Kidney Plasma Membranes on Glucose Transport Inhibition by IgG.

Adsorption experiments were performed to determine if the inhibitory effect of the 4IgG fractions from the IDDM patients on 3-0-methyl-β-D-glucose transport in islet cells could be adsorbed by preincubation with cells or cell membranes that do and do not express the glucose transporter shared by liver and β-cells. Four mg of IgG from 4 IDDM patients was incubated with 20,000 islet cells, 20 mg hepatocyte membranes (cells that normally share the same glucose transporter), and 20 mg of plasma membranes from rat erythrocytes and renal tubular cell brush borders (neither of which contain this transporter). As shown in FIG. 6, the inhibitory effect was abolished by preincubation of the IgG with islet cells and hepatocyte membranes but not by preincubation with erythrocyte or brush border membranes.

C. Discussion and Implications

The findings exemplified by studies such as the foregoing, are consistent with the inventors' conclusion that autoimmune attacks on β-cells include attacks on either a β-cell glucose transporter per se or some other associated protein somehow involved in glucose transport. The studies show that IgGs obtained from the sera of humans with new-onset IDDM inhibit initial rates of 3MG uptake into dispersed rat islets of Langerhans. The inhibition of 3MG uptake by islets treated with these IgGs does not appear to be a generalized reduction in islet cell permeability since the uptake of L-leucine by these cells in unaffected.

The possibility of nonspecific toxic effects of β-cell antibodies on β-cell viability as the explanation for these findings is excluded by the fact that nonviable cells do not sediment through the dibutyl phthalate layer of the assay tubes and are therefore not measured. Furthermore, the fact that L-glucose permeability was unaffected by the diabetic IgG indicates the integrity of the permeability barrier of these cell preparations.

Treatment of hepatocytes and erythrocytes with IgG from IDDM patients did not affect 3MG uptake into these cells. Thorens, et al. have shown that the erythrocyte glucose transport protein has a 55% sequence homology with the glucose transporter of liver indicating structural differences between the two proteins (21). Antibodies to a synthetic peptide deduced from the sequence of the liver transporter recognize a protein of β-cells of islets, suggesting that these transporters may be similar in structure (18). The lack of an effect of IgG from new-onset IDDM patients upon glucose transport by hepatocytes was surprising and may indicate that small structural differences between the β-cell transporter and the liver transporter do exist. Alternatively, IgG from new-onset IDDM patients might recognize an antigen other than the transporter that is somehow functionally involved in 3MG uptake.

The results of the present invention suggest that islet cells have a transporter which is similar kinetically to the liver transporter, and that IgG fractions from IDDM patients exert their inhibitory effects preferentially on this high Km transporter. The fact that the inhibitory effect on 3-0-methyl-β-D-glucose uptake by islet cells was abolished by preincubation with both islet cells and hepatocyte membranes, but not by erythrocyte or kidney tubule brush border membrane preparations, provides support for the interpretation that the liver and β-cell transporters are similar. The failure of IgG from IDDM patients to inhibit glucose transport by hepatocytes may indicate an excess of glucose transporter relative to the concentration of putative antibody.

Antibodies to at least three different islet antigens have been found in serum of patients at the time of diagnosis of IDDM. These antigens are the 64 kd membrane protein of Bedkkeskov et al.(5), cytoplasmic islet cell antigens (22), and insulin (20). However, there is no reason to believe that the 64 kd protein is related to the 55 kd glucose transporter. Tests for cytoplasmic autoantibodies were negative in almost half of the IDDM patients who IgG inhibited 3MG transport activity. Although insulin autoantibodies were not assayed in the IDDM patients, we established that preincubation of islet cells with insulin antibodies had no effect on 3-0-methyl-β-D-glucose uptake.

The functional implications of a 50% reduction in 3-0-methyl-β-D-glucose uptake by islet cells are unclear. Glucose transport capacity far exceeds the capacity to phosphorylate glucose (5), suggesting that this degree of interference with glucose transport is probably not sufficient to affect insulin secretion in vivo. However, the IgG concentrations used were 20% of those, on a protein-to-cell ratio basis, used by Kanatsuna, et al.(4) to demonstrate IgG-induced inhibition of insulin secretion by islets. Also it should be noted that 3-0-methyl-β-D-glucose uptake differs kinetically from β-cells (12) and which do not express the livertype glucose transporter. This could well have minimized the inhibition. Nevertheless, the inventors consider it unlikely that the antibody-induced inhibition of in vitro glucose uptake is the cause of the loss of glucose-stimulated insulin secretion in vivo.

Even though there is no reason to assume that the putative glucose transporter antibodies are cytotoxic to β-cells, it is conceivable that they initiate a chain of events leading to loss of glucose-stimulated insulin release. Alternatively they may be an epiphenomenon, an immune response to release of β-cell antigens following destruction of β-cells by an unidentified process.

REFERENCES

1. Lernmark et al. (1981), *Diabetology*, 21:431–35.
2. Ora et al. (1976), *Pro. Natl. Acad. Sci. U.S.A.*, 73:1338–42.
3. Srikanta et al. (1983), *N. Engl. Jrnl. Med.*, 308:322–25.
4. Kanatsuna et al. (1981), *Diabetes*, 30:231–34.
5. Baekeskov et al. (1982), *Nature*, 298:167–69.
6. Baekeskov et al. (1987), *J. Clin. Invest.*, 79:926–34.
7. Christie et al. (1988), *Diabetologia*, 31:591–602.
8. Ey et al. (1978), *Immunochem.*, 15:429–436.
9. Krell and Rabin (1984), *Diabetes*, 33: 703–11.
10. Naber et al. (1980), *Diabetologia*, 19:439–44.
11. Casten (1981), "Rotman and Papermasters Technic for Fluorochroming Viable Cells using FDA." In: Clark G, ed. *Staining Procedures*, 4th ed. Baltimore: Williams and Wilkin, pp. 93–94.
12. Gorus et al. (1984), *J. Biol. Chem.*, 259:1196–1200.
13. Steck and Kant (1974), *Meth. Enzymol.*, 31:172–180.
14. Axelrod and Pilch (1983), *Biochemistry*, 22:222–27.
15. Kaunitz and Wright (1984), *J. Membr. Biol.*, 79:41–51.
16. Wheeler et al. (1981), *J. Biol. Chem.*, 256:8907–14.
17. Hellman et al. (1971), *Biochim. Biophys. Acta*, 241:147–54.
18. Orci et al. (1989), *Science*, 245:295–297.
19. Berson et al. (1956), *S. Clin. Invest.*, 35:170.
20. Palmer et al. (1983), *Science*, 223:1337–39.
21. Thorens et al. (1988), *Cell*, 55:281–90.
22. Botazzo et al. (1974), *Lancet*, 2:1297–83.
23. Ashcroft and Nino (1978), *Biochim. Biophys. Acta*, 538:334–42.

Modifications and alterations will become apparent to skilled artisans in light of the foregoing disclosure. It is intended by the inventors that all such modifications and changes be included within the scope of the subject matter which the present applicants regard as their invention, and as defined by the following claims.

What is claimed is:

1. A method for diagnosing autoimmune insulin dependent diabetes mellitus, comprising the steps of:

(a) obtaining a sample of serum from a patient suspected of having autoimmune IDDM;

(b) testing for the presence of an autoimmune immunoglobulin in the patient's serum the immunoglobulin being characterized by its ability to interfere with the glucose transporting activity of pancreatic islet cell glucose transporter, the presence of such an immunoglobulin in the patient's serum being diagnostic of autoimmune IDDM, wherein testing for the presence of the immunoglobulin comprises:

(i) preparing an admixture which includes the islet cell glucose transporter and serum from the patient;

(ii) incubating the admixture under conditions appropriate for the formation of immunocomplexes; and (iii) testing for the formation of immunocomplexes between the islet cell glucose transporter and the serum immunoglobulins, to determine the presence of the autoimmune immunoglobulin therein.

2. The method of claim 1, wherein IgG is prepared from the patient's immunoglobulin, and the IgG is employed to prepare the admixture of step (a).

* * * * *